(12) United States Patent
Callister et al.

(10) Patent No.: US 7,087,026 B2
(45) Date of Patent: Aug. 8, 2006

(54) DEVICES AND METHODS FOR MEASURING BLOOD FLOW RATE OR CARDIAC OUTPUT AND FOR HEATING OR COOLING THE BODY

(75) Inventors: Jeffrey P. Callister, Redwood City, CA (US); Timothy R. Machold, Moss Beach, CA (US)

(73) Assignee: Radiant Medical, Inc., Redwood City, CA (US)

( * ) Notice: Subject to any disclaimer, the term of this patent is extended or adjusted under 35 U.S.C. 154(b) by 486 days.

(21) Appl. No.: 10/394,505

(22) Filed: Mar. 21, 2003

(65) Prior Publication Data

US 2003/0225336 A1    Dec. 4, 2003

Related U.S. Application Data

(60) Provisional application No. 60/366,282, filed on Mar. 21, 2002.

(51) Int. Cl.
*A61B 5/02* (2006.01)

(52) U.S. Cl. .................................. 600/526; 600/504
(58) Field of Classification Search ................. 600/526
See application file for complete search history.

(56) References Cited

U.S. PATENT DOCUMENTS

| | | | |
|---|---|---|---|
| 4,819,655 A * | 4/1989 | Webler | 600/526 |
| 4,941,475 A * | 7/1990 | Williams et al. | 600/505 |
| 5,217,019 A | 6/1993 | Hughes | |
| 5,271,410 A | 12/1993 | Wolzinger et al. | |
| 5,285,796 A * | 2/1994 | Hughes | 600/481 |
| 5,509,424 A * | 4/1996 | Al-Ali | 600/505 |
| 5,579,778 A * | 12/1996 | Baker et al. | 600/504 |
| 5,588,438 A | 12/1996 | McKown et al. | |
| 5,682,899 A * | 11/1997 | Nashef et al. | 600/505 |
| 5,692,514 A * | 12/1997 | Bowman | 600/504 |
| 5,788,647 A | 8/1998 | Eggers | |
| 5,807,269 A | 9/1998 | Quinn et al. | |
| 5,837,003 A | 11/1998 | Ginsburg | |
| 5,954,659 A * | 9/1999 | Curley et al. | 600/505 |
| 6,394,961 B1 | 5/2002 | Pfeiffer et al. | |
| 6,416,533 B1 | 7/2002 | Gobin et al. | |
| 6,497,721 B1 | 12/2002 | Gindburg et al. | |

FOREIGN PATENT DOCUMENTS

| | | | |
|---|---|---|---|
| WO | WO 91/17703 | * | 11/1991 |
| WO | WO 01/58397 | | 8/2001 |
| WO | WO 01/58397 A1 | | 8/2001 |

* cited by examiner

*Primary Examiner*—Max Hindenburg
*Assistant Examiner*—Patricia C. Mallari
(74) *Attorney, Agent, or Firm*—Robert D. Buyan; Stout, UXA, Buyan & Mullins, LLP

(57) ABSTRACT

Heat exchanger-equipped catheters and related methods that are useable for changing or maintaining at least a portion of the body of a human or veterinary patient at a desired temperature and for the measurement of cardiac output or blood flow rate within a blood vessel, without the need for introduction of saline solution or any other foreign substance into the patient's blood.

43 Claims, 6 Drawing Sheets

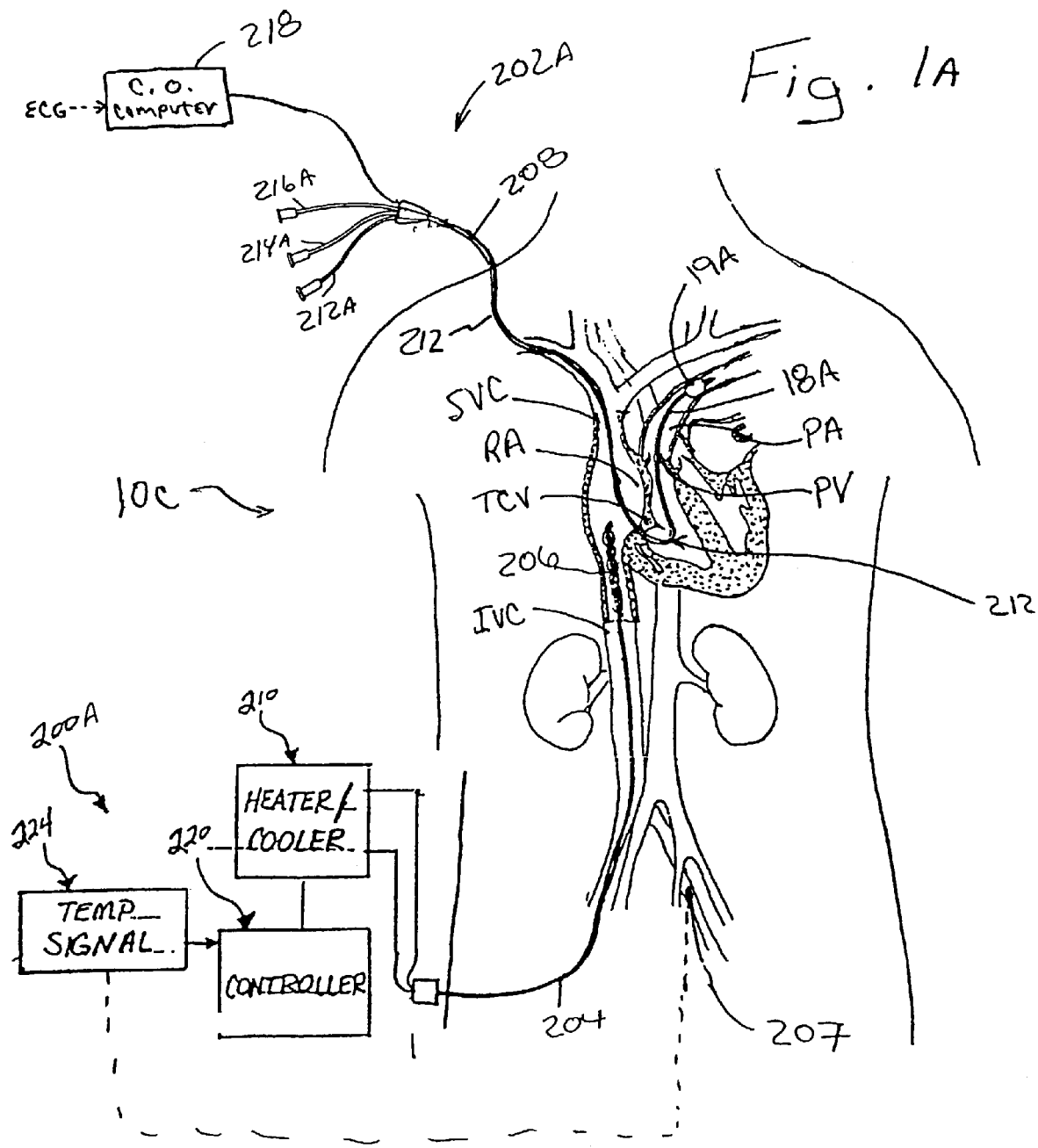

DEVICES AND METHODS FOR MEASURING BLOOD FLOW RATE OR CARDIAC OUTPUT AND FOR HEATING OR COOLING THE BODY

RELATED APPLICATION

This application claims priority to U.S. Provisional Patent Application No. 60/366,282 filed on Mar. 21, 2002, the entirety of which is expressly incorporated herein by reference.

FIELD OF THE INVENTION

This invention relates generally to methods and apparatus for medical treatment and more particularly to methods, devices and systems for heating or cooling the body and for measuring the flow rate of blood or cardiac output, as well as other physiologic variables, in mammalian patients.

BACKGROUND OF THE INVENTION

In many clinical situations, it is desirable for physicians to monitor a patient's cardiac output. Typically, a patient's cardiac output is expressed in terms of the volume (in liters) of blood ejected by the left ventricle of the patient's heart within a one minute period. In a mathematical sense, cardiac output (CO) may be defined as the product of heart rate (HR) and stroke volume (SV), as follows:

$$HR \text{ (heartbeats per minute)} \times SV \text{ (liters per heartbeat)} = CO \text{ (liters per minute)}$$

Various techniques have been used for measurement of cardiac output, including direct measurement methods as well as indirect measurement methods. Typical methods for direct measurement of cardiac output include thermodilution and indicator dye dilution. Typical methods for indirect measurement of cardiac output include thoracic bioimpedance, Doppler ultrasound and a technique known as the Fick method whereby cardiac output is calculated using a formula that is based on the measured oxygen contents of samples of mixed venous blood (i.e., blood obtained from the patient's pulmonary artery) and arterial blood (i.e., blood obtained from one of the patient's arteries) as well as the measured carbon dioxide ($CO_2$) content in air expired from the patient's lungs.

The thermodilution method for measuring cardiac output is frequently used in clinical practice. Typically, thermodilution cardiac output measurements are carried out through the use of a special type of catheter known as a Swan Gantz right heart catheter, sometimes referred to as a pulmonary artery or "PA" catheter or thermodilution catheter. The Swan Gantz right heart catheter is a balloon-tipped catheter that is inserted into a vein (typically the internal jugular vein, external jugular vein, subclavian vein or brachial vein) and initially advanced to a first position where the catheter's distal tip is positioned in the right atrium of the patient's heart. While the catheter is in this first position the balloon located near the catheter's distal tip is inflated. The flowing blood then carries the inflated balloon (and the distal end of the catheter) through the right atrium, through the tricuspid valve, through the right ventricle, through the pulmonic valve and finally to a second position wherein the distal tip of the catheter is situated in the patient's pulmonary artery. This procedure is sometimes referred to as "flow directed" catheter placement. After the distal end of the catheter has been flow directed into the pulmonary artery, the balloon is deflated. Thereafter, as the catheter remains indwelling, the balloon may occasionally re-inflated for brief periods of time to facilitate measurement of a variable known as "pulmonary artery wedge pressure." This is accomplished by causing the balloon to substantially block flow through the pulmonary artery and then obtaining a pressure reading within the pulmonary artery, distal to the inflated balloon.

A thermistor is located near the distal end of the catheter. The thermistor is connected to a cardiac output computer. The thermistor may be a fully sleeved, single beaded thermistor made of nickel alloy insulated with polyimide (Sensors of these types are available from, for example, Biosensors International Pte Ltd 1995). Bead thermistors of this type can provide good stability and, in at least some cases, provide accuracy similar to that of more expensive platinum resistance thermometers (PRTs). Bead thermistors are also relatively fast and able to monitor temperature changes over a very short period of time, a characteristic that may be useful in the thermodilution method of determining CO.

A proximal injectate port is formed in the portion of the catheter that resides in the right atrium or vena cava when the catheter's distal tip is in the pulmonary artery. When it is desired to measure cardiac output, a bolus (e.g., 10 cc) of room temperature or cooled injectate (e.g., saline solution or 5% dextrose in water) is injected through the proximal injectate port, becomes mixed with the flowing blood and is carried through the right ventricle and through the pulmonary artery. As the cooled blood/injectate mixture passes the thermistor, the thermistor's resistance changes. The amount of change in resistance is proportional to the change in blood temperature. A voltage across the thermistor generates a small current. That current changes as the temperature sensed by the thermistor changes and, thus, generates a signal representing the temperature sensed by the thermistor. The cardiac output computer receives the temperature signal from the thermistor and, on the basis of the change in temperature monitored by the thermistor following injection of the injectate, calculates cardiac output (liters per minute). For example, the injection of a bolus of cold fluid may mix with the blood and create a bolus of cold blood which will cause a transient rise in temperature as the blood passes the thermistor in the PA, and the time in which the temperature sensor detects a rise in temperature will determine how fast that bolus of blood is passing by the thermistor, i.e. velocity of the blood flow, from which the CO can be determined.

In addition to facilitating measurement of cardiac output by thermodilution, the typical Swan Gantz catheters (i.e., pulmonary artery catheters) have also incorporated multiple working lumens that terminate in ports located at various location on the catheter body. These lumens and their accompanying ports are useable for infusion of fluids, withdrawal of blood samples and for monitoring of blood pressures and pressure wave forms at various locations in the right heart. For example, samples may be taken of venous blood from a proximal port located in the vena cava or right atrium, or mixed venous blood samples from a distal port located in the pulmonary artery. Also, for example, central venous pressure (CVP) may be monitored through the proximal port located in the vena cava or right atrium, right ventricular pressure (RVP) may be monitored through a medial port located in the right ventricle, pulmonary artery pressure (PAP) may be monitored (while the balloon is deflated) through the distal port located in the pulmonary artery and pulmonary artery wedge pressure (PAP-W) may be monitored (while the balloon is inflated) through the distal port located in the pulmonary artery.

The traditional Swan Gantz or PA catheters have required that a bolus of injectate (e.g., cool 0.9% NaCl solution) be injected into and mixed with the patient's blood each time it is desired to obtain a reading of cardiac output. Such bolus injections of saline solution or other injectate can be problematic. For example, if the patient is hypothermic, it can be necessary to ice or refrigerate the injectate prior to its introduction into the body in order to ensure that the injectate temperature is sufficiently different from the blood temperature to provide a meaningful cardiac output computation. Also, in cases where the proximal injectate port of the Swan Ganz catheter remains inside of the introducer sheath some portion of the injectate bolus may flow in the retrograde direction within the sheath, thereby resulting in delivery of less than the full bolus volume to the pulmonary artery and a resultant error in the cardiac output determined. Also, in patients who are hypertensive or very ill, the volume and chemical composition of the injectate can cause undesired effects on the patient's electrolyte balance, state of hydration, blood pressure, etc.

Recognizing the potential problems associated with repeated bolus injections of saline solution or other injectate for the purpose of thermodilution cardiac output measurements, others have described "injectateless" thermodilution catheters wherein heat is exchanged between the catheter and the flowing blood in a manner that can allegedly be detected by a thermistor located in the pulmonary artery and from which the patient's cardiac output can be computed, but which does not require the introduction of any foreign substance into the blood. Examples of such "injectateless" thermodilution catheters include those described in U.S. Pat. No. 4,941,475 (Williams et al.) entitled Thermodilution By Heat Exchange and U.S. Pat. No. 5,807,269 (Quinn et al) entitled Thermodilution Catheter Having A Safe, Flexible Heating Element. Although these prior art "injectateless" thermodilution catheters may be useable for measuring or estimating cardiac output and for other purposes typically required of catheters of this type, these prior art devices are not believed to be optimal for use in all patients and/or for all clinical purposes. Thermodilution cardiac output catheters are typically not designed for, or capable of, substantially changing the body temperature of the patient, as such is not their intended purpose. There are also significant risks and negative health consequences associated with floating a catheter through the heart and into the PA. Accordingly, there remains a need in the art for the development of new "injectateless" catheters and related devices/methods for measuring cardiac output.

SUMMARY OF THE INVENTION

In a basic embodiment, the present invention provides heat exchanger-equipped catheters and related methods that are useable for changing or maintaining at least a portion of the body of a human or veterinary patient at a desired temperature and for the measurement of cardiac output or blood flow rate within a blood vessel, without the need for introduction of saline solution or any other foreign substance into the patient's blood. This may be done without the need of an additional stick if done in conjunction with an endovascular heat exchange catheter, such as the type typically used for inducing or reversing mild hypothermia. Examples of such endovascular heat exchange catheters are described in various United States Patents, including U.S. Pat. Nos. 6,527,789; 6,497,721; 6,436,131; 4,428,563; 6,306,161; 6,264,679; 6,231,594; 6,149,673; 6,110,168, 6,126,684, 6,096,068 and 5,837,003, each of which is expressly incorporated herein by reference. If the amount of heat introduced (or removed) from the blood is determined for a given time, and the change in temperature of the blood before the heat is added (or removed) the flow rate of the blood (i.e. the CO) can be easily determined.

Similarly, the rate of heat exchange between a particular heat exchange catheter is highly dependent on the rate of flow of blood over the heat exchange element, and if the catheter is adequately characterized, the rate of flow over the heat exchange element can be determined from the rate of heat exchange. This may be a computation from the data available or may be in the form of a look-up table consulted when the rate of heat exchange with the blood is determined.

In any case wherein an endovascular heat exchange catheter is used to determine CO, the determination of CO may be simultaneous with the induction of mild hypothermia or other desired temperature management. In such cases the only "stick" administered may be to insert the endovascular heat exchange catheter. Where the endovascular heat exchange catheter is part of a system that includes a computerized controller, the necessary computational elements such as a cardiac output computer for thermodilution or a computerized "look-up" table can be included in the controller.

In more complex embodiments, the present invention provides pulmonary artery catheters, devices, systems and methods useable for a) measuring cardiac output without the injection of saline solution or any other foreign substance into the patient's blood, b) measuring of right heart pressures (e.g., CVP, RVP, PAP, PAP-W), c) infusion of fluids and withdrawal of blood samples (e.g., venous blood samples from a proximal port located in the vena cava or right atrium, mixed venous blood samples from a distal port located in the pulmonary artery) and, optionally may perform other functions such as d) delivery of electrical current to the hear for purposes of pacing, defibrillation or diagnostic electrophysiology.

BRIEF DESCRIPTION OF THE APPENDICES AND DRAWINGS

Appendix A is a worksheet setting forth a method by which blood flow rate or cardiac output may be determined without actually measuring or determining the power or wattage of heat exchanger and a method for adjusting the computed cardiac output to account for differences in the characterization of heat exchanger fluid and blood.

Appendix B is a diagram illustrating a method for using a characterized heat exchange balloon and look-up table(s) or databases to determine cardiac output.

Figure 1:
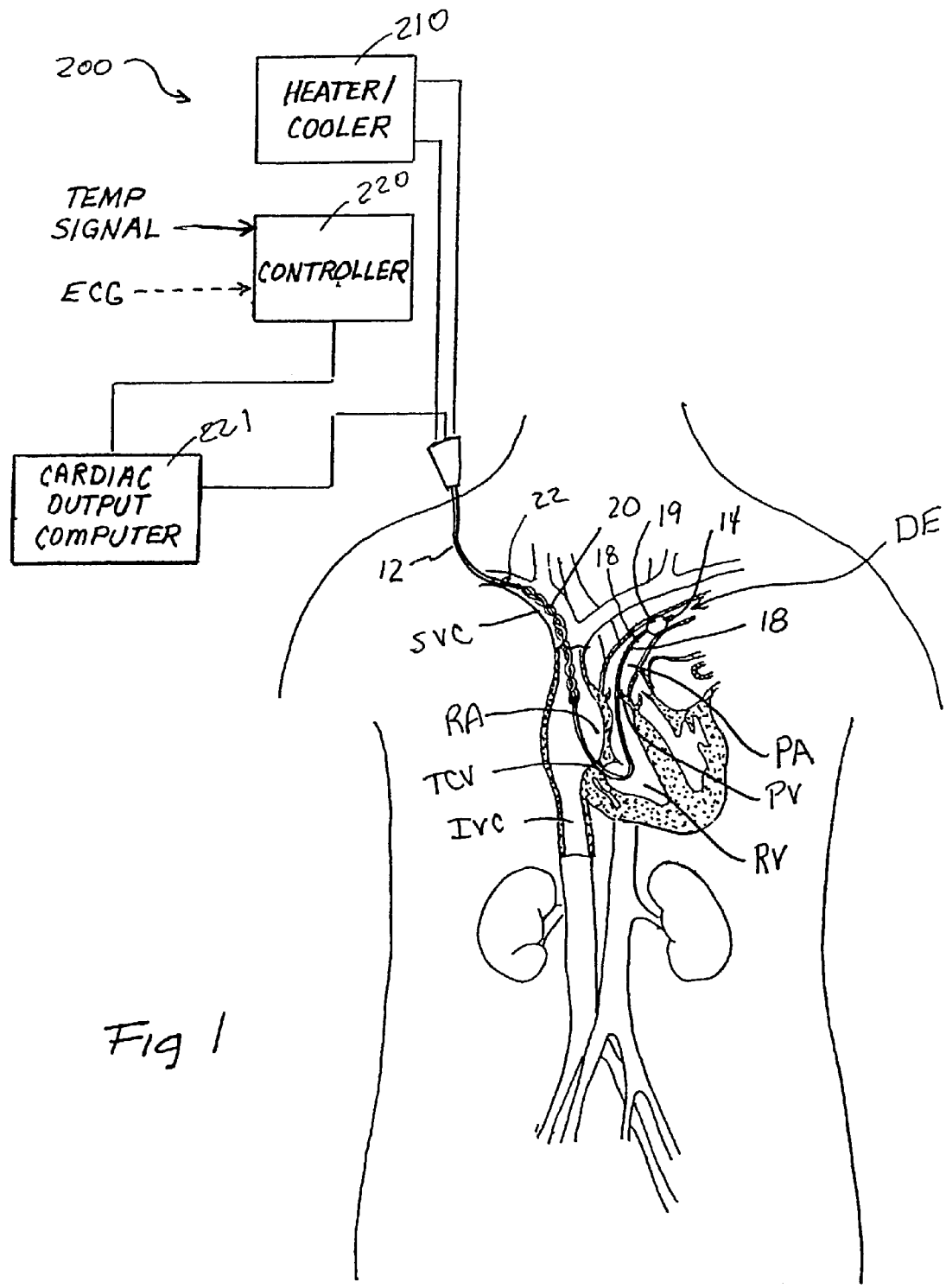
FIG. 1 is a schematic diagram of a first embodiment of the present invention wherein a single catheter is used to measure the patient's cardiac output and to heat or cool the patient's body.
Figure 1B:
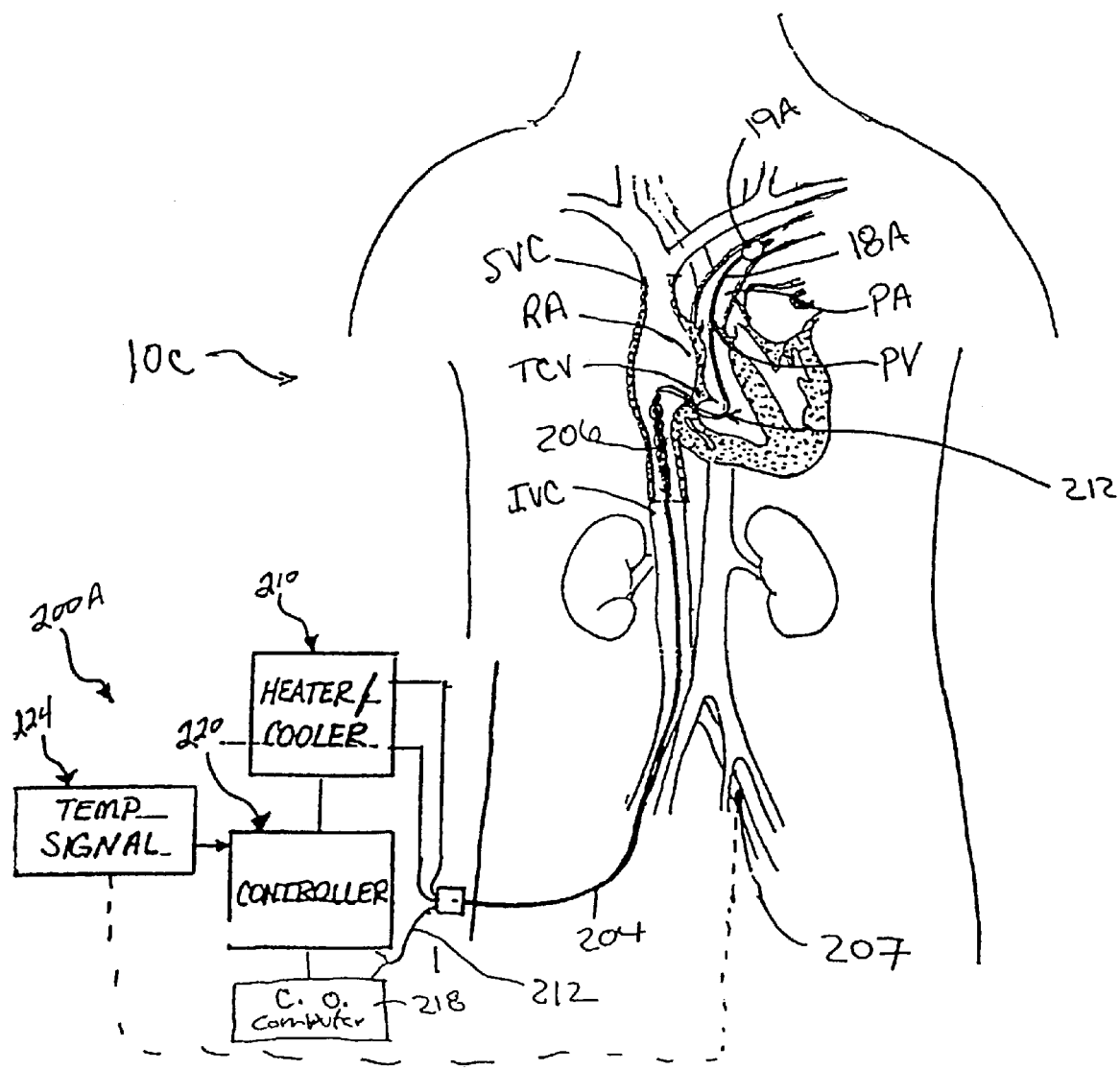
FIG. 1a is a schematic diagram of a second embodiment of the present invention wherein two (2) catheters are used to measure the patient's cardiac output and to heat or cool the patient's body.

FIG. 1b is a schematic diagram of a third embodiment of the present invention wherein a heat exchange catheters is positioned within the patient's inferior vena cava and a smaller pulmonary artery catheter or thermistor equipped guide wire like probe is advanced through the heat exchange catheter, through the right heart and into the patient's pulmonary artery, thereby providing a system that may be used to measure the patient's cardiac output and to heat or cool the patient's body.

Figure 2:
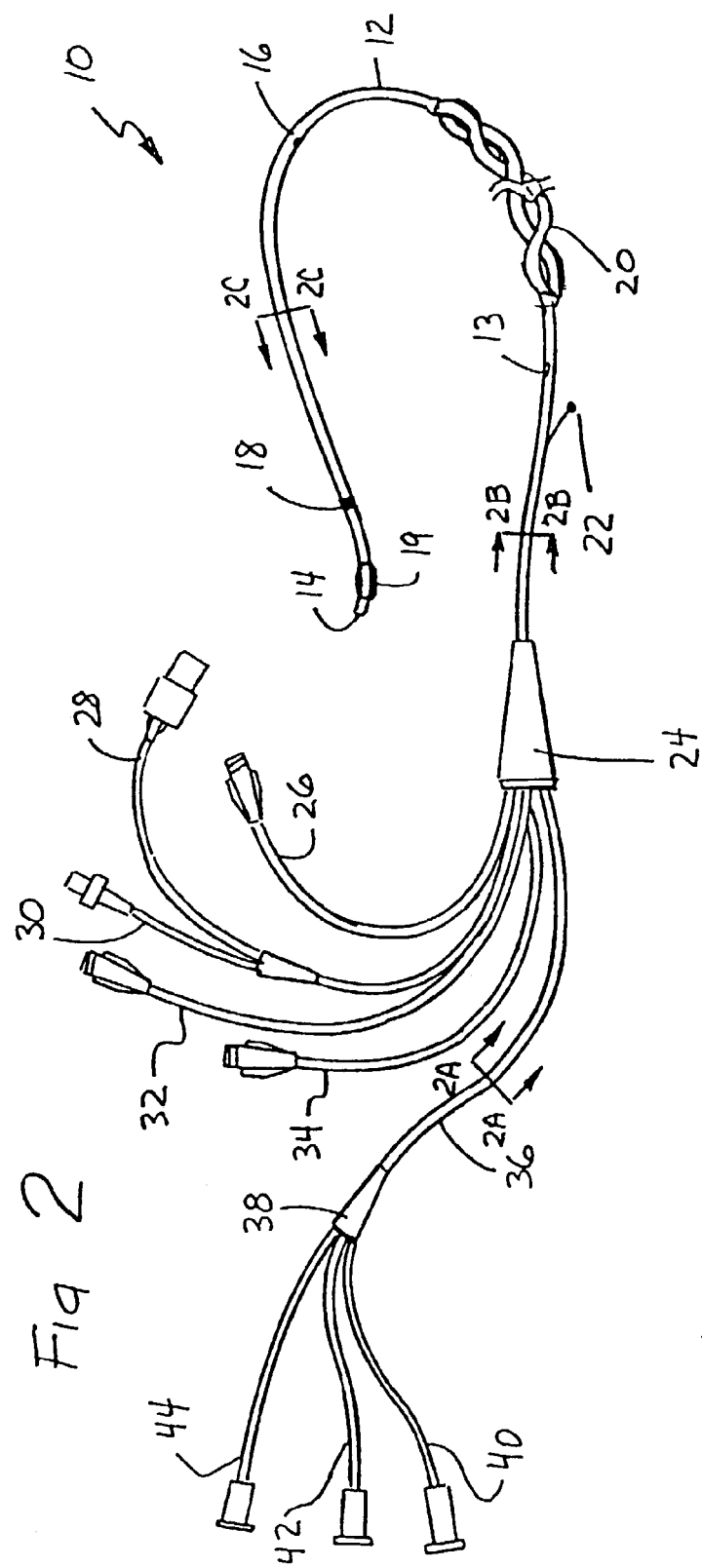

FIG. 2 is a perspective view of a heat exchanger-equipped pulmonary artery catheter of the present invention.

Figure 2A:
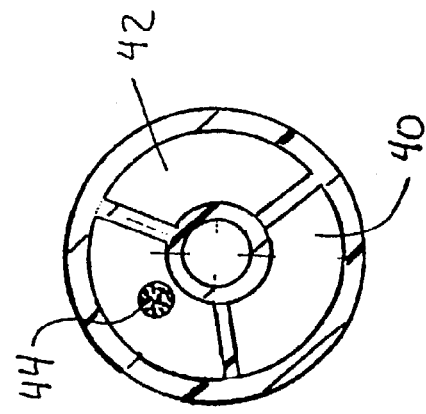

FIG. 2A is a cross-sectional view through line 2A—2A of FIG. 2.

Figure 2B:
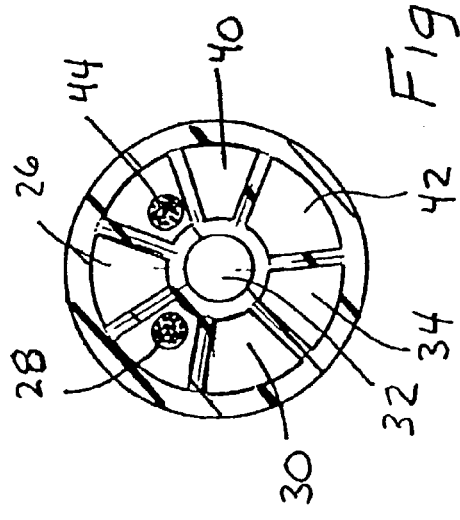

FIG. 2B is a cross-sectional view through line 2B—2B of FIG. 2.

Figure 2C:
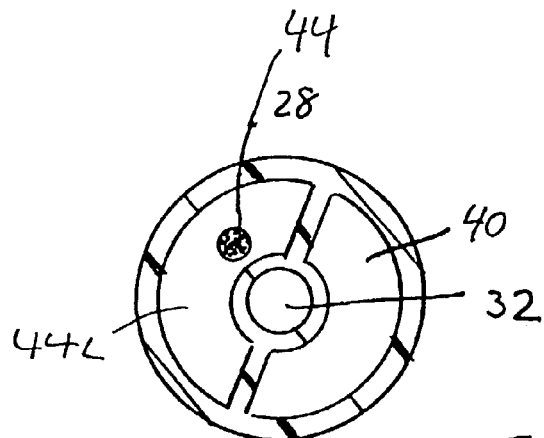

FIG. 2C is a cross-sectional view through line 2C—2C of FIG. 2.

Figure 3:
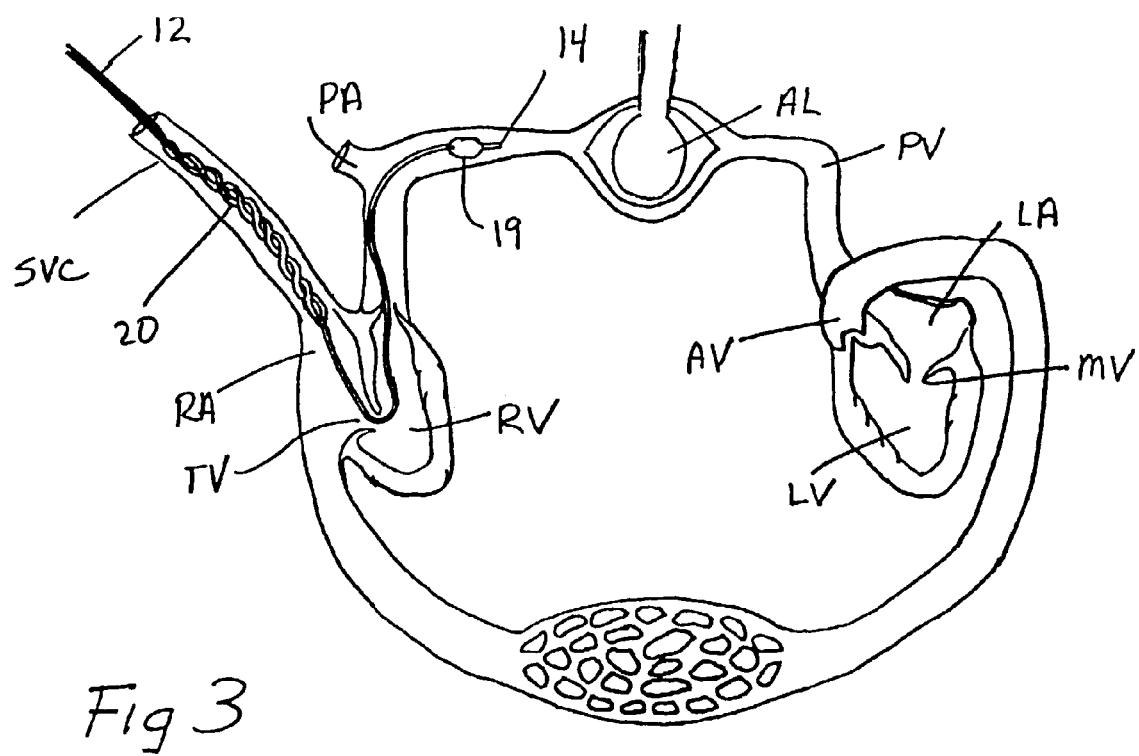

FIG. 3 is a conceptual diagram of a heat exchanger-equipped pulmonary artery catheter device of the present invention operatively positioned for use in a) measuring cardiac output, b) measuring right heart and pulmonary artery pressures and c) heating or cooling the patient's body.

Figure 4:
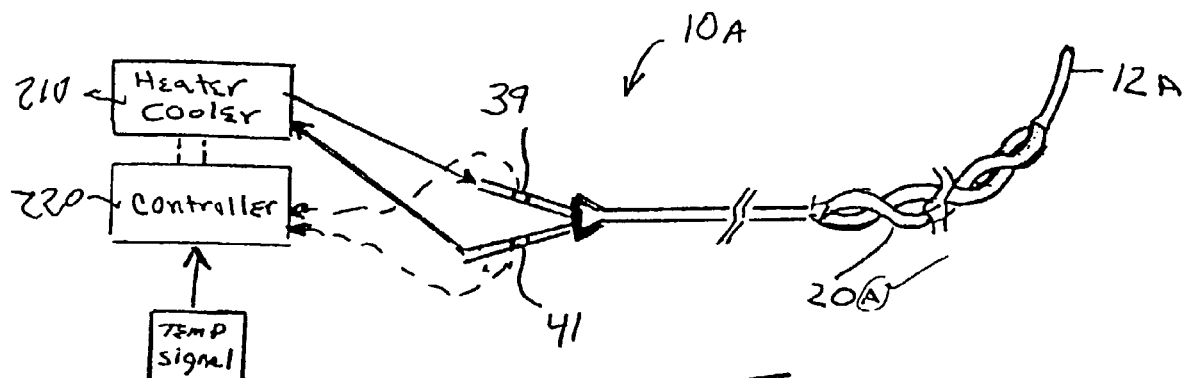

FIG. 4 is a schematic diagram of a basic heat-exchanger equipped catheter of the present invention having sensors for monitoring the temperature of heat exchange fluid flowing into and out of the heat exchanger.

Figure 5:
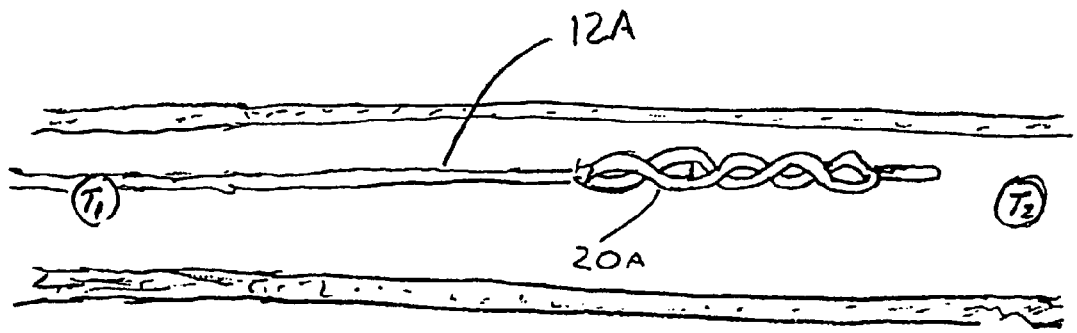

FIG. 5 is a schematic diagram of a basic heat-exchanger equipped catheter of the present invention having temperature sensors for determining the temperature of the patient's blood upstream and downstream of the heat exchange.

DETAILED DESCRIPTION AND EXAMPLES

The following detailed description, and the accompanying drawings to which it refers, are provided describing and illustrating certain examples or specific embodiments of the invention only and not for the purpose of exhaustively describing all possible embodiments and examples of the invention. Thus, this detailed description does not in any way limit the scope of the inventions claimed in this patent application or in any patent(s) issuing form this or any related application.

Heating/Cooling of the Body and Cardiac Output Measurement Using a Single Catheter FIGS. 1 and 3 show schematic diagrams of a heat exchanger-equipped pulmonary artery catheter device 10 of the present invention that is useable for heating or cooling all or a portion of the patient's body and also for measuring cardiac output without the injection of saline solution or any other foreign substance into the patient's blood. Additionally, this catheter device 10 may optionally be equipped and useable for measuring of right heart pressures (e.g., CVP, RVP, PAP, PAP-W), infusing fluids and withdrawing of blood samples (e.g., venous blood samples from a proximal port located in the vena cava or right atrium, mixed venous blood samples from a distal port located in the pulmonary artery). Also, this catheter device 10 may optionally be equipped to perform other functions such the delivery of electrical current to the heart or to specific locations on the heart muscle for purposes of pacing, defibrillation or diagnostic electrophysiology.

As shown in the schematic diagrams of FIGS. 1 and 3, a catheter device 10 comprising an elongate flexible catheter body 12, a heat exchanger 20, a balloon 19, a first or distal temperature sensor 18 (e.g., a thermistor) and a second or proximal temperature sensor 22 (e.g., another thermistor) is positioned as shown, with the heat exchange element 20 in the subclavian vein and perhaps partially within the right atrium, with the distal end DE of the catheter body 12 in the patient's pulmonary artery PA. In the particular example shown in FIG. 1 the catheter device 10 was placed in this operative position by first percutaneously inserting the distal end DE of the catheter body 12 into the subclavian vein SCV. However various alternative venous entry sites may be used including the internal jugular vein, external jugular vein, brachial vein or femoral vein. A particular example is shown in FIG. 1B, wherein the catheter is inserted into the femoral vein. After insertion, the catheter body 12 is advanced first position where the catheter body's distal end DE is positioned in or near the right atrium RA of the patient's heart. Thereafter, while the catheter is in this first position the balloon 19 located near the catheter body's distal end DE is partially inflated and the pressure of the flowing blood then carries the partially inflated balloon 19 and the distal end of the catheter body through the right atrium RA, through the tricuspid valve TCV, through the right ventricle RV, through the pulmonic valve PV and finally to the second or operative position shown in FIG. 1, wherein the distal end DE of the catheter body 12 including the balloon 19 and a first temperature sensor (e.g., a thermistor) 18 are situated within the patient's pulmonary artery PA and the heat exchanger 20 is positioned within the superior vena cava SVC adjacent to the right atrium RA. After the catheter body has been flow directed to this second or operative position, the balloon 19 is deflated to allow relatively normal flow through the pulmonary artery PA. The catheter body 12 is connected to various extracorporeal apparatus including a heater/cooler 210 for alternately heating and cooling the heat exchanger 20, a programable controller 220, and a cardiac output computer apparatus 221. The second or proximal temperature sensor 22 is in communication with the controller 220 such that a temperature signal indicative of the blood temperature proximal to or upstream of the heat exchanger 20 is continually monitored or at times determined by the second or proximal temperature sensor 22. To avoid interference with the temperature sensor 22, as may result from hot or cold fluid flowing through the catheter body 12 near the sensor 22, the temperature sensor 22 may be deployed away from the catheter body 12 by any of several means, for example those shown in co-owned and co-pending U.S. patent application Ser. No. 09/905,389, which is incorporated here by reference.

The signal or signals from the second or proximal temperature sensor 22 is/are communicated by hard wired connection or wireless connection to the controller. Within the heater/cooler 210 or elsewhere in the system are heat exchange sensor(s) (not shown in FIG. 1) which monitor or sense the amount of heat being exchanged between the heat exchanger 20 and the blood flowing past the heat exchanger 20. As shown in FIG. 5, in embodiments where the heat exchanger 20 is a flowing fluid type of heat exchanger, temperature sensors 39, 41 may be placed on inlet and outlet lines through which heat exchange fluid flows into and out of the heat exchanger 20. The flow rate of heat exchange fluid through the catheter may also be sensed by a flow meter of any of various kinds (not shown in FIG. 1a) located anywhere along the flow path of the heat exchange fluid. The rate of heat exchange may be calculated from the difference between the temperature of the fluid flowing into the heat exchanger and the temperature of the fluid flowing out of the heat exchanger and the rate of flow of the heat exchange fluid. Signals from these sensors 39, 41 are also communicated to the controller 220 by hard wired or wireless connection and the controller 220 may be programed to compute the amount of heat exchanged during the relevant time period. The amount of heat exchanged between the heat exchanger and the blood may be calculated by the following formula:

$$q = m \cdot (t_{in} - t_{out})K$$

wherein q=heat exchange, m=flow rate of heat exchange fluid through the heat exchanger, $t_{in}$=temperature of heat exchange fluid entering the heat exchanger, $t_{out}$=temperature of heat exchange fluid exiting the heat exchanger and K=the thermal constant of the heat exchanger fluid.

The first or distal temperature sensor 18 is also in communication with the controller 220 such that a temperature signal indicative of the blood temperature in the pulmonary artery PA (distal to or downstream of the heat exchanger) may be continually monitored or sampled at various times by the first or distal temperature sensor 18. The signal or signals from the first or distal temperature sensor 18 is/are communicated by hard wired connection or wireless connection to the controller 220. The controller 220 is additionally programmed to determine the difference between the blood temperature upstream of the heat exchanger 20 as determined by the second temperature sensor 22 and the blood temperature downstream of the heat exchanger (in the pulmonary artery PA) as sensed by the first or distal temperature sensor 18. A cardiac output computer 221, which may be incorporated into and integrated with the controller 220 or may be a separate device, receives signals indicative of the blood temperature and heat exchange data and then calculates cardiac output (CO) by an appropriate formula, such as the following:

$$CO = \text{Heat Exchanged} \div \Delta t$$

wherein CO=cardiac output (the amount of blood passing through the right heart per unit time), Heat Exchanged=the amount of heat added to or removed from the blood via the heat exchanger 20 per unit time and Δt=the difference between the temperature of the patient's blood before it undergoes heat exchange with the heat exchanger 20 as measured by the second temperature sensor 13 and the temperature of blood flowing through the patient's pulmonary artery as measured by the first temperature sensor 14.

It will be appreciated by those of skill in the art that the catheter device 10 may optionally include one or more pressure sensors and/or working lumens and/or ports to facilitate infusion of fluids, withdrawal of blood samples and/or monitoring of local blood pressures at various locations within the right heart. These aspects of the catheter device 10 shown in FIGS. 1 and 3 are specifically shown in the more detailed views of FIGS. 2–2c. With reference to FIGS. 2–2c, this embodiment of the catheter body 12 incorporates multiple optional lumens 28L, 30, 32, 34, 40, 42 and 44L as well as multiple ports 13, 14, 16. The lumens continue out of a proximal member 34 as separate proximal tubes 37 having Luer connectors or other types of connectors at their proximal ends.

An alternative to having a balloon located on the distal end of the catheter itself as is shown in FIGS. 1 and 1A is illustrated in FIG. 1B. A pulmonary artery temperature probe which may be in the form of a guidewire GW having a temperature sensor 18b on its distal end DE is advanced into the PA. The guidewire may be flexible and have an inflatable balloon at its distal end for floating placement as described above. Alternatively it may have a shape that facilitates the location of its distal end in the PA when it is advanced into the heart. That shape may be imparted to the guidewire in numerous ways, for example by using a heat sensitive, shape memory metal such as Nitinol. The distal balloon may be usable to acquire wedge pressures. Alternatively the guidewire may have at its distal end, in addition to the temperature sensor, a pressure transducer 19b to determine wedge pressures without the need to insert a balloon into the PA. This may reduce the diameter of the device that needs to be advanced into the PA since no balloon structure needs to be advanced and no lumen needs to be incorporated into the guidewire shaft to inflate the balloon.

As shown in FIG. 2, one of the lumens that extends through the catheter body 12 and proximal tubes 37 may be a guidewire/pulmonary artery lumen 32 which extends through the catheter body and opens through a distal port 14 in the distal end DE of the catheter body 12. This guidewire/pulmonary artery lumen 32 may be initially used to advance the catheter device 10 over a pre-inserted guidewire. Thereafter, after the catheter body 12 has been positioned in its operative position as shown in FIG. 1, the guidewire may be removed and pulmonary artery pressure (PAP) and pulmonary artery wedge pressure (PAP-W) may be monitored though lumen 32 and port 14 by attaching a pressure transducer to the Luer connector on the proximal end of the proximal extension tube 37 of lumen 32. Also, when it is desired to obtain samples of mixed venous blood from the pulmonary artery PA, such samples may be withdrawn through lumen 32 and port 14. Another lumen 44L may carry a proximal or second temperature sensor wire 44 to connect the proximal or second temperature sensor 18 to the controller 220 and/or cardiac output computer 221. The proximal or second temperature may be mounted on a wire or other member 23 which springs or moves outwardly away from the catheter body 12 to hold the temperature sensor 22 sufficiently far away from the catheter body to eliminate or minimize any effect of the heat exchange fluid flowing through the proximal catheter body 12 to or from the heat exchanger, thereby providing a more accurate reading of the blood temperature upstream of the heat exchanger. Alternatively, the controller 220 may be programmed to apply a correction factor, based on the temperature(s) and flow rates of the heat exchange fluid flowing through the proximal catheter body 12 to or from the heat exchanger, to negate or minimize any effect of such flowing heat exchange fluid on the blood temperature sensed by the proximal or second temperature sensor 13.

A balloon inflation/deflation lumen 30 extends through the catheter body 12 and through one of the proximal tubes 37 to allow inflation and deflation of the balloon 19. A balloon inflation or pressure indicator (not shown) may be mounted on or integrated into the connector on the proximal end of the extension tube 37 of lumen 30 to indicate the degree to which the balloon 19 is inflated at any given point in time. An optional proximal working lumen 34 may open through a proximal port 13 which is located within the right atrium RA or adjacent vena cava when the catheter body 12 is in its operative position as shown in FIG. 1. This proximal working lumen 34 and port 13 may be connected to a pressure transducer and used for monitoring of central venous pressure CVP. Also, this proximal working lumen 34 and port 13 may be used as a central intravenous line for central administration of drugs, fluids or other substances and/or for withdrawal of non-mixed venous blood samples. An optional medial working lumen 26 may open through a medial port 16 which is located within the right ventricle RV when the catheter body 12 is in its operative position as shown in FIG. 1. Such medial working lumen 26 may be used for monitoring of right ventricular pressures or for other access to the right ventricle. Heat exchange fluid is pumped into and out of the heat exchanger 20 through heat exchange inflow lumen 40 and heat exchange outflow lumen 42. Temperature sensors may be positioned within these lumens 40, 42 on or adjacent to the Luer connectors at the proximal ends of the extension tubes 37 through which lumens 40, 42 extend or elsewhere to provide temperature measurements of the heat exchange fluid flowing into and out of the heat exchanger 20. These temperature measurements may then be used to calculate the amount of heat exchanged between the heat exchanger 20 and the patient's blood, as explained above.

In this embodiment, the heat exchange catheter system may be used to simultaneously heat or cool all or a portion of the patient's body to a desired temperature, while determining CO. The temperature of the patient is altered by the endovascular heat exchanger 20, for example the heat exchanger 20 may induce mild hypothermia, the thermal mass of the patient is so large that the change in body temperature is slow enough that it does not significantly impact the determination of CO in accordance with this invention. In addition, the temperature measured at the first temperature sensor 22 would be that of the incoming blood, generally the body temperature, and the temperature measured at the second temperature sensor 18 would be the temperature of the blood immediately after the heat exchange, and the relevant measure is the difference of the two temperatures, ΔT and thus a change in body temperature would not affect this. Although this might affect the rate of heat exchange somewhat and thus affect the "look-up" table method described below, this affect would be small and would not significantly affect the value of the information obtained.

Heating/Cooling of the Body and Cardiac Output Measurement Using Multiple Catheters As an alternative to the method and system described above and shown in FIGS. 1 and 2–2d, an alternative method and system is shown in FIG. 1a. In the alternative method and system of FIG. 1a, two (2) separate catheter devices are used, a heat exchange catheter device 200a and a pulmonary artery catheter device 202a. The heat exchange catheter device 200a comprises a heat exchange catheter 204, a body temperature sensor 207 and related extracorporeal control and operation apparatus 210, 220. The heat exchange catheter 206 has a heat exchanger 206 positioned thereon, and may be any suitable type of heat exchanger including any of those described in U.S. Pat. No. 5,486,208 (Ginsburg), PCT International Publication WO 00/10494 (Machold et al.), U.S. Pat. No. 6,264,679 (Keller et al.), U.S. patent application Ser. No. 09/777,612, all of which are expressly incorporated herein by reference.

The extracorporeal apparatus useable in conjunction with the heat exchange catheter 204 include a heater/cooler 210 and controller 220 of as described above with respect to the single catheter embodiment.

The body temperature sensor 207 may be positioned on or in the heat exchange catheter 204 or may be a separate apparatus, such as a small thermistor-equipped catheter that is inserted into a blood vessel other than blood vessel in which the heat exchange catheter 204 is positioned. When the body temperature sensor 207 is positioned in a separate catheter, such will eliminate any potential for interference with the accurate sensing of blood temperature by the circulation of heated or cooled heat exchange fluid through the proximal portion of the heat exchange catheter. In embodiments where the body temperature sensor 207 is incorporated into or positioned on the heat exchange catheter 204 it will be positioned proximal to or upstream of the heat exchanger 206 and may be insulated or positioned on a wire or member that deploys the body temperature sensor 207 away from the proximal shaft of the heat exchange catheter 204, such as the proximal or second temperature sensor 202 described above in connection with the single catheter 10 device.

The pulmonary artery device 202a comprises a catheter 208 and an extracorporeal computation apparatus for computing cardiac output. The pulmonary artery catheter 208 of this embodiment comprises an elongate, flexible catheter having a balloon 19a and pulmonary artery temperature sensor 18a that are substantially the same as those described above in connection with the single catheter 10 device. This pulmonary artery catheter 208 may be passed through the right heart and into the pulmonary artery PA by the same flow-directed placement technique described above with respect to the single catheter 10 device. Optionally, this pulmonary artery catheter 208 may include other lumens and ports for accessing, infusing fluids into, monitoring pressures (e.g., CVP, RVP, PAP, PAP-W) or withdrawing blood samples (venous, mixed venous), from various locations within the right heart. For example, this pulmonary artery catheter my optionally include a proximal (central venous) lumen and port 34, 13, a medial (right ventricular) working lumen and port, 26, 16 and a distal (pulmonary artery) lumen and port 32, 14 as described above with respect to the single catheter 10 device.

In this embodiment also, the heat exchange catheter system 200a may be used to simultaneously heat or cool all or a portion of the patient's body to a desired temperature while determining CO. While the heat exchange catheter is exchanging heat with the body, the rate of heat being exchanged between the blood and the heat exchanger may be determined by the same formula and the same technique as described above in connection with the single catheter 10 device. Thereafter, the patient's cardiac output may likewise be determined by the formula:

$$CO = \text{Heat Exchanged} \div \Delta t$$

wherein CO=cardiac output (the amount of blood passing through the right heart per unit time), Heat Exchanged=the amount of heat added to or removed from the blood via the heat exchanger 206 per unit time and Δt=the difference between the temperature of the patient's blood before it undergoes heat exchange with the heat exchanger 20 as measured by the body temperature sensor 207 and the temperature of blood flowing through the patient's pulmonary artery as measured by the pulmonary artery temperature sensor 119a on the pulmonary artery catheter 208.

It will be appreciated that the extracorporeal cardiac output computer 218 of this embodiment may comprise a stand alone device or may be incorporated into or integrated with the controller 220. Similarly, the heater/cooler may be housed within a common console or housing with the controller and (optionally) the cardiac output computer, thereby providing a unitary extracorporeal system for use during the procedure.

Another variation of the two-catheter technique is shown in FIG. 1b. In this embodiment of the invention, a heat exchange catheter 204 as described above is inserted into a femoral vein and advanced to a position where its heat exchanger 206 is positioned within the inferior vena cava IVC. A lumen extends longitudinally through the heat exchange catheter 204 and may be used to advance the heat exchange catheter 204 over a guidewire. After the heat exchange catheter 204 is in the position shown in FIG. 1b, the guidewire (if used) is removed and a pulmonary artery probe 207 is advanced through the central lumen of the heat exchange catheter and out of its distal end. The pulmonary artery probe 207 may comprise any flexible elongate member such as a catheter, guide wire, wire or the like. A balloon 19b and temperature sensor 18b are located on the pulmonary artery probe, near its distal end. The pulmonary artery probe 207 is advanced to a position in or near the right atrium, its balloon 19b is partially inflated and the flow-directed technique described above is used to float the distal end of the pulmonary artery probe 207 through the right heart and into the patient's pulmonary artery. Thereafter, the temperature sensor 18b of the pulmonary artery probe 207 may be used to facilitate cardiac output measurements in the same manner as described herein with respect to FIGS. 1 and 1a. In some embodiments, the pulmonary artery probe 207 may include a lumen that extends through a port distal to the balloon 19b or a pressure sensor, such as an electronic or fiber optic pressure sensor, distal to the balloon 19b such that pulmonary artery pressure PAP and pulmonary artery wedge pressure PAP-W may be measured in addition to the ability to measure cardiac output.

Heating Cooling of the Body and Local Blood Flow Determination

It is to be further appreciated that the devices and systems of the present invention are not only useable for determination of cardiac output, but rather are broadly useable for determining blood flow through any blood vessel or the flow rate of any fluid through any body conduit or catheter. In this regard, when it is desired to measure local flow rate withing a blood vessel, conduit or catheter, there is no need for placement of a catheter within the pulmonary artery, rather a heat exchange catheter is placed in the desired blood vessel, conduit or catheter and an upstream temperature $T_1$ and a downstream temperature $T_2$, as shown schematically in Appendix A. The amount of heat exchanged between the heat exchanger 20a and the blood or other flowing fluid is determined as described above with respect to both the single catheter and dual catheter cardiac output determination methods. Thereafter, the flow rate of blood or fluid through the blood vessel, conduit or catheter is determined by the formula:

Flow Rate=Heat Exchanged÷Δt wherein the Flow rate is defined as the volume of blood or other fluid flowing past the heat exchanger per unit time, the Heat Exchanged=the amount of heat added to or removed from the blood or fluid via the heat exchanger 20a per unit time and Δt=the difference between the upstream temperature $T_1$ of the blood or fluid and the downstream temperature $T_2$ of the blood or fluid.

EXAMPLE 1

A Single Catheter System used for Endovascular Induction/Maintenance of Hypothermia and Periodic Cardiac Output/Right Heart Pressure Determinations A human patient suffering from a myocardial infarction is admitted to a critical unit of a hospital. A heat exchanger-equipped pulmonary artery catheter 10 of the type described above and shown in FIGS. 1 and 2–2c is percutaneously inserted into the patient's right subclavian vein using a Seidinger technique. Optionally, a guidewire may be advanced into the patient's superior vena cava and the proximal end of that guidewire is inserted into the distal port 14 of the catheter and through the guidewire/pulmonary artery lumen 32. The catheter body 12 is then advanced over the guidewire to a first position where its distal end DE is positioned within or immediately adjacent to the patient's right atrium RA. The guidewire, if used, is removed. The guidewire/pulmonary artery lumen 32 is filled with saline solution or other suitable fluid and the proximal connector of lumen 32 is attached to a physiological pressure transducer (not shown) and the pressure tracing for that transducer is displayed on a monitor (not shown). The positioning of the distal port 14 catheter 10 in or adjacent to the right atrium RA is then verifiable by visualization of a typical right atrial waveform on the monitor. The balloon 19 is then partially inflated to a diameter that is small enough to pass through the tricuspid and pulmonic valves TCV, PV. The operator then slowly advances the catheter as the force of the flowing blood directs the balloon 19 and distal end DE of the catheter through the right atrium RA, through the tricuspid valve TCV, through the right ventricle RV, through the pulmonic valve PV and into a second or operative position within the pulmonary artery PA. The position of the distal end DE of the catheter in the pulmonary artery is initially verified by deflation of the balloon 19 and observance of a typical pulmonary artery wave form on the monitor followed by full inflation of the balloon such that it coapts firmly with the wall of the pulmonary artery and observance of a typical pulmonary artery wedge pressure tracing on the monitor. While the catheter body 12 has been positioned in its second or operative position as shown in FIG. 1, the heat exchanger 20 will be positioned in the superior vena cava SVC, the proximal port 13 (optional) will be positioned in the right atrium RA and the medial port 16 (optional) will be positioned in the right ventricle RV. Saline or other suitable fluid may also be placed in the optional proximal working lumen 34 and central venous pressure (CVP) may be monitored through proximal port 13 such that a tracing of CVP may be displayed on the monitor, if desired. Similarly, saline or other suitable fluid may also be placed in the optional medial working lumen 26 and right ventricular pressure (RVP) may be monitored through medial port 16 and a tracing of RVP may be displayed on the monitor. Final verification of the proper positioning of the catheter body 12 in the second or operative position is preferably accomplished by chest x-ray or other suitable radiographic imaging.

The heat exchanger 20 is connected to the heater/cooler 210. The heater/cooler 210 and the proximal thermister 22 are in communication with the controller 220. In this example, the proximal thermister 22 indicates that the patient's body temperature is normothermic at 37° C. In this example, it is desired to cool the patients body to a temperature of approximately 32° C. Thus, the operator inputs the desired 32° C. body temperature into the controller 220 and actuates the system. The heater/cooler 210 then pumps heated and or cooled saline solution through the heat exchanger 20, as necessary, to cause the proximal thermister to read approximately 32° C. and the thereafter maintain such desired approximate body temperature. This mild hypothermia may lessen the severity of cardiac muscle damage that occurs as a result of the myocardial infarction. If the patient is awake and alert, one or more anti-shivering treatments or anti-shivering drugs may be administered to prevent or lessen the shivering and discomfort that the patient may experience as a result of the catheter-induced hypothermia.

In addition to the above-described cooling of the patient's body, the catheter 10 may also be used to measure cardiac output. When it is desired to measure cardiac output, the controller 220 will receive signals from temperature sensors within the system indicating the temperature of the saline solution being pumped into the heat exchanger (Temp In) and the temperature of the saline solution being returned from the heat exchanger (Temp Out). From this information, the controller then calculates a $\Delta t_{saline}$. The controller 220 also senses the flow rate of the heat exchange fluid (Flow$_{saline}$) and uses that flow rate and $\Delta t_{saline}$ to calculate the rate of heat exchanged between the heat exchanger 20 and the blood (referred to as "Heat Exchanged"). For example, if the Temp In is 4.7° C. and the Temp Out is 10.4° C. the $\Delta t_{saline}$ is 5.7° C. The flowrate (M) at which the saline solution is pumped through the heat exchanger 20 is constant at 500 ml/min or 0.5 liters/m or 8.33 ml/sec. Thus, the Heat Exchanged is 200 watts. After receiving these data, the controller 220 computes Cardiac Output as follows:

Power=flow rate/$\Delta T$ where power is measured in watts, k flow rate is ml/sec. And $\Delta t$ is degrees Centigrade. In the example above the power is about 200 watts.

The heat received(or given up) by the blood will always be the same as the heat given up (or received) by the heat exchange fluid in any period of time, i.e. power in equals power out, in this case 200 watts. Therefore a determination of cardiac output may be made if the temperature before the heat exchange is measured and the temperature of the mixed blood after the heat exchange is measured. For example, if the temperature before the heat exchange is 36.70 and the temperature after the heat exchange measured (e.g. by a PA temperature sensor) and determined to be 35.66, it would result in a $\Delta t_{blood}$ of 1.14° C. Using this information and the knowledge that the heat exchange that generated the 1.14° C. is 200 watts, the flow of the blood (i.e. cardiac output) can be determined. In this case it would be: 200 watts/1.14 degrees C.=47.76 ml ° C./sec×(1/1.14° C.)=2.51 liters/minute. Thus, the patient's cardiac output in this example is 2.51 liters/min.

There are other factors, of course that may vary the determined cardiac output. For example, for the purposes of this example we have assumed that the blood and the saline have the same specific heat, that is that one calorie of heat from the saline will lower the temperature of the blood the same amount that the temperature of the saline was raised by the heat exchange. We have also assumed that the density of the two fluids is the same, that is that 1 ml of saline has the same number of grams as 1 ml blood. Finally, we have also assumed that the relative density of the fluids does not change with changes in temperature. These assumptions are not necessarily correct, and the adjustment factors can readily be made, but for ease of explanation these relatively small factors have been ignored for the purpose of this example.

With the assumptions that the two liquids are essentially the same, a simple computation is possible. Of Power in=Power out, and flow is equal to power divided by $\Delta t_{saline}$, then the ration of ($\Delta t_{saline}$/Flow(saline)=$\Delta t_{blood}$/Flow (blood), and if both $\Delta t_{saline}$ and $\Delta t_{blood}$ as well as Flow (saline) are known, the flow of the blood is easily determined regardless of fluctuations or changes in power.

$$CO \times \Delta T_{Blood}/0.95 = \text{Flow}_{saline} \times \Delta T_{saline}/0.99$$

$$CO = \text{Flow}_{saline} \times \Delta T_{saline} \times 0.95/(0.99 \times \Delta T_{Blood})$$

$$CO = 0.5 \text{ML/MIN} \times 5.6° \text{ C.} \times 0.95/(0.99 \times 1.14° \text{C.}) = 2.35 \text{ l/min}$$

The constant for the specific heats of two fluids will remain constant and can be built in to the calculations for CO made by the controller with the assumption that the density and specific heat of the blood and the saline are known. The sterile, physiologic saline will generally not vary. Blood may vary between individuals, at various times in the same individual, and even at different temperatures, but the magnitude of variability will generally be small. Thus, a clinically valuable approximation of cardiac output is obtained even when these variables are ignored.

EXAMPLE 2

Determination of CO by Rate of Heat Exchange

It is possible to make a determination of blood flow in a vessel and thus indirectly CO without the need to measure the temperature of the blood before the heat exchange and after the heat exchange. For a given heat exchange region located in a blood stream, directly proportional to the blood flow across the heat exchange region. Thus if the heat exchange increases and all other factors stay the same, that indicates that the blood flow has increased. The same, of course, holds true if the heat exchange decreases; that indicates that the blood flow has decreased. This phenomenon allows one to determine the blood flow if the heat exchange region is adequately characterized and the amount of heat exchanged in a given length of time is known. As has been previously described, in a heat exchange catheter as illustrated in FIG. 1 or 1A, where the amount of heat exchanged with the blood can be determined by measuring the rate of flow of the heat exchange fluid and the difference of the input temperature and the output temperature. If the heat exchange region has been adequately characterized, the velocity of the blood flow can be calculated. If catheters are used that are all similar in heat exchange characteristics, a look-up table can be created wherein the determination of the wattage exchanged with the blood (which may be determined by multiplying the change in temperature of the heat exchange fluid with the flow rate of the heat exchange fluid) then the velocity of blood flowing over the heat exchange region may be derived by looking up the value on a table created using catheters of the type in use.

This information by itself may have value to a treating physician. For example it would allow the physician to see if the velocity was within a normal range. It would also be possible, with certain assumptions that are generally accurate, to use that information to determine cardiac output. For example, it would be necessary to know the diameter of the vessel in order to determine the volume of flow at a certain velocity. However, if the height of the patient is known, and the vessel in which the heat exchange region is located is known (for example the IVC) then it would be possible to determine, within a range, what the diameter of that vessel would be and thus determine the amount of blood flow in the IVC. With the additional assumption that the total CO is derived ⅓ from the SVC and ⅔ from the IVC, this would translate very conveniently into CO. While the accuracy would tend to decrease with each additional assumption, it generally would still be accurate enough to be useful.

For example, in the fluid flow heat exchange catheter illustrated in FIG. 1 and described in greater detail in application Ser. No. 09/777,612 incorporated herein in full by reference, the wattage exchanged with the blood may be determined by measuring the flow rate of the heat exchange fluid, measuring the temperature of the fluid flowing into the catheter and measuring the temperature of the fluid flowing out of the catheter to determine a $\Delta T$, and multiplying the flow rate times the $\Delta T$. For example, if the fluid is flowing at the rate of 500 ml/min. and the temperature of the fluid entering the catheter is 5° C. and the temperature of the fluid after exchanging heat with the blood is 10.8° C. and the flow rate of the fluid is 500 ml/min, then the wattage exchanged with the blood is 200 Watts. (One Watt is 0.2388 cal./sec.;

1 cal. is 1 ml ° C.) With the flow rate measured, and the ΔT measured, the wattage can be determined, and with a catheter having known heat exchange characteristics, a look-up table can give the rate of flow over the heat exchange surface. With certain assumptions such as the size of the vessel and the contribution of the flow of that vessel to the total cardiac output, a figure may be determined for cardiac output.

Changes in cardiac output, that is changes in the velocity of blood flow over the heat exchange region, dramatically affect the amount of wattage exchanged with the blood. For example, referring to Table 1 below, if the heat exchange fluid in the catheter is flowing at a rate of 500 ml/min, and the heat being exchanged with the blood is 290.4 watts, the look-up table shows that the blood is following at a rate of 3.6 liters per minute. If the wattage drops to 236.6 watts, the blood flow is determined to be only 1.8 liters per minute.

In practical application, the determination of cardiac output by this method will generally be less precise than direct measurement by thermodilution, but for the purposes of monitoring patient condition and making medical treatment decisions, the information may be valuable and helpful even if not precise. Indeed, such information may be clinically useful, even if the blood flow rate measured in the vessel in which the catheter is positioned is different from actual CO. For example, even if the measured flowrate is different from CO, such measured flowrate would nonetheless be expected to vary concurrently with, and in relative magnitude to, changes in CO. Thus, the measured flowrate may indicate whether CO is remaining stable, increasing, decreasing and/or if CO changes so significantly as to indicate a potential problem or "alarm" situation. The advantages of determining the information without the need of an additional stick other than the heat exchange catheter and without the need to insert anything into the heart or the PA will often exceed the disadvantage of slightly less precision.

TABLE 1

DATA BASE CORRELATING FLOWRATE OF HEAT EXCHANGE FLUID AND HEAT TRANSFER (WATTS) TO BLOOD FLOW

| Blood Flow | Catheter Flow | Heat Trans (Watts ▯Total Length) |
|---|---|---|
| 3.6 Lit/min | 500 ml/min | 190.4 |
| 3.0 Lit/min | 500 ml/min | 179.8 |
| 2.4 Lit/min | 500 ml/min | 156.8 |

This embodiment of the invention wherein the blood flow rate or cardiac output is determined using a look-up table or database is further exemplified by that set forth in Appendix B.

Although exemplary embodiments of the invention have been shown and described, many changes, modifications and substitutions may be made by those having ordinary skill in the art without necessarily departing from the spirit and scope of this invention. For example, elements, components or attributes of one embodiment or example may be combined with or may replace elements, components or attributes of another embodiment or example to whatever extent is possible without causing the embodiment or example so modified to become unuseable for its intended purpose. Accordingly, it is intended that all such additions, deletions, modifications and variations be included within the scope of the following claims.

Although several illustrative examples of means for practicing the invention are described above, these examples are by no means exhaustive of all possible means for practicing the invention. The scope of the invention should therefore be determined with reference to the appended claims, along with the full range of equivalents to which those clams are entitled.

APPENDIX A

One method described herein provides the following method for computing the CO if the $\Delta T_{Blood}$, the $Flow_{saline}$ and the $\Delta t_{saline}$ are determined.

Power In=Power out $Flow_{saline}$=Power In/$\Delta T_{saline}$

Power In=$Flow_{saline} \times \Delta T_{saline}$ $Flow_{Blood}$=Power Out/$\Delta T_{blood}$ Power In=Power Out so CO (which is $Flow_{Blood}) \times \Delta T_{Blood}$=$Flow_{saline} \times \Delta T_{saline}$ $CO=\Delta T_{saline}/\Delta T_{Blood} \times Flow_{saline}$ Thus, where the saline flow is 500 ml/min and the delta T for saline is 5.6° C., and the delta T for the blood is 1.14° C., the CO would be:

5.6° C./1.14° C.×0.50 l/min=2.46 l/min

It is not necessary in this example to determine wattage. If wattage changes for any reason, for example if the heat flow between the catheter and the blood is dramatically effected by the change of CO, as long as the sensors can determine the $\Delta T_{Blood}$, the $Flow_{saline}$ and the $\Delta T_{saline}$, an accurate CO can be determined.

This formula assumes that the density of blood times the specific heat of blood and of saline are the same. They are close, but not identical. A factor that accounts for the density of the fluid and the specific heat of the fluid may be determined; we will call that factor w. That factor for saline may be, for example 0.99 compared to water, whereas blood may be, for example, 0.95 blood compared to water. This will create an adjustment factor to correct the determination of flow which is the ration of the w for blood and the w for saline. In the example above, and using the factors stated:

$CO$=Power×0.95/$\Delta T_{Blood}$; Power=$CO \times \Delta T_{Blood}$/0.95

$Flow_{saline}$=Power×0.99/$\Delta T_{saline}$; Power=$Flow_{saline} \times \Delta T_{saline}$/0.99

$CO \times \Delta T_{Blood}$/0.95=$Flow_{saline} \times \Delta T_{saline}$/0.99

$CO$=$Flow_{saline} \times \Delta T_{saline} \times 0.95/(0.99 \times \Delta T_{Blood})$ $CO$=0.5ML/MIN×5.6_C×0.95/(0.99×1.14_C)=2.35 l/min The constant for the specific heat of two fluids will always be the same and can be built in to the calculations for CO made by the controller with the assumption that the density and specific heat of the blood and the saline are known. The sterile, physiologic saline will generally not vary. Blood may vary between individuals, at various times in the same individual, and even at different temperatures, but the magnitude of variability will generally be small. For purposes of this application we will ignore these variabilities.

APPENDIX B

1. Characterize balloon and create look-up table of watts of energy exchanged for a given velocity of blood flow over the catheter.
2. Create a look-up table for the typical size of the IVC or other relevant vessel for a given size patient.
3. Insert the characterized balloon into the patient.
4. Input the patient size.*
5. Measure the rate of heat exchange by the characterized heat exchange catheter (e.g. measure the temperature of the heat exchange fluid in and heat exchange fluid out of catheter, or measure the electrical power required to maintain the heat exchange fluid at a given temperature).
6. Determine the blood flow velocity from the look-up table.
7. Determine the IVC size from the look-up table.*
8. Calculate the CO from the blood flow velocity and the IVC size.
9. Display the CO.

* These steps may be replaced by an actual input value of the size of the IVC or relevant vessel is actually measured, for example by angiography, and the actual value input.

What is claimed is:

1. A method for determining cardiac output or discerning a substantial change in cardiac output in a mammalian patient, the method comprising the steps of:
   A) providing a heat exchange catheter that comprises an elongate catheter body having a heat exchanger positioned thereon;
   B) inserting the heat exchange catheter into the vasculature of the patient and positioning the heat exchanger within a blood vessel through which the blood flow rate is substantially the same as or bears a known relationship to cardiac output;
   C) causing heat to be exchanged between the heat exchanger and blood flowing past the heat exchanger;
   D) determining the amount of heat exchanged between the heat exchanger and the blood within a time period;
   E) determining the flow rate of blood past the heat exchanger based on the amount of heat exchanged in the time period, the flow rate of blood being determined by reference to a database which correlates flow rate values to corresponding amounts of heat exchange measured in Step D for blood in vessels having different luminal diameters; and
   F) computing at least an estimate of cardiac output or discerning a change in cardiac output, on the basis of the flow rate determined in Step E.

2. A method according to claim 1 wherein Step C is carried out such that the amount of heat exchanged between the heat exchanger and the blood results in a change in the temperature of all or part of a patient's body so as to induce hypothermia, induce hyperthermia, maintain normothermia or achieve and maintain a temperature that is different from that patient's normothermic temperature.

3. A method according to claim 1 wherein Step B comprises positioning the heat exchanger in a vessel through which venous blood flows, the venous blood flow through that vessel accounting for at least 15% of the total blood flow entering the right atrium.

4. A method according to claim 1 wherein the flow rate of blood is determined in Step E by the following formula:

$CO = \text{Heat Exchanged} \div \Delta t$ wherein CO=the amount of blood passing through the right heart per unit time, Heat Exchanged=the amount of heat added to or removed from the blood per unit time and Δt=the difference between the temperature of the patient's blood before it undergoes heat exchange with the heat exchanger as measured by a second temperature measuring device and the temperature of blood flowing after it undergoes heat exchange with the heat exchanger through the patient's pulmonary artery as measured by a first temperature measuring device.

5. A method according to claim 4 wherein the luminal diameter of the vessel in which the heat exchanger is positioned is estimated based on the height and weight of the patient.

6. A method according to claim 4 wherein the luminal diameter of the vessel in which the heat exchanger is positioned is measured.

7. A method according to claim 6 wherein the luminal diameter of the vessel in which the heat exchanger is positioned is measured on an image of the vessel obtained by an imaging technique selected from the group consisting of:
   fluoroscopy;
   ultrasound imaging;
   intravascular ultrasound imaging;
   magnetic resonance imaging;
   computed tomographic imaging;
   angiography; and,
   X-ray.

8. A method according to claim 1 wherein the heat exchanger is positioned in the venous vasculature and wherein a computed or estimated cardiac output is calculated in Step F by multiplying the flow rate determined in Step E by a factor representing the portion of total venous blood flow through the right heart that comes from the vessel in which the heat exchanger is positioned.

9. A method according to claim 8 wherein at least a portion of the heat exchanger is positioned in the inferior vena cave and the factor applied for that portion of the heat exchanger is approximately ⅔.

10. A method according to claim 8 wherein at least a portion of the heat exchanger is positioned in the inferior vena cave and the factor applied for that portion of the heat exchanger is approximately ⅓.

11. A method according to claim 8 wherein at least a portion of the heat exchanger is positioned in the right atrium and the factor applied for that portion of the heat exchanger is 100%.

12. A method according to claim 9 wherein the amount of heat exchanged between the heat exchanger and the blood is determined by the formula:

$q = m \cdot (t_{in} - t_{out}) K$ wherein q=heat exchange, m=flow rate of heat exchange fluid through the heat exchanger, $t_{in}$=temperature of heat exchange fluid entering the heat exchanger, $t_{out}$=temperature of heat exchange fluid exiting the heat exchanger and K=the thermal constant of the heat exchanger fluid.

13. A method according to claim 1 wherein the catheter device provided in Step A has a heat exchanger through which a heat exchange fluid is circulated and wherein the amount of heat exchanged between the heat exchanger and the blood within a time period is calculated based on the flow rate of the heat exchange fluid, the temperature of the heat exchange fluid entering the heat exchanger and the temperature of fluid exiting the heat exchanger over the time period.

14. A method according to claim 1 wherein the catheter device provided in Step A has a heat exchanger which receives power from an external power supply apparatus, and the determination of the heat exchanged between the heat exchanger and the blood is determined by measuring the power output by the power supply apparatus.

15. A method according to claim 1 wherein the catheter device provided in Step A has a heat exchanger through which a heat exchange fluid is circulated and wherein the amount of heat exchanged between the heat exchanger and the blood within a time period is calculated based on the amount of power consumed by an external unit.

16. A method according to claim 1 wherein the method further comprises the steps of:
measuring the temperature of blood downstream of the heat exchanger;
measuring the temperature of blood upstream of the heat exchanger; and, wherein,
the amount of heat exchanged in the time period is determined in Step D by the formula:

downstream temperature−upstream temperature.

17. A method according to claim 16 wherein the temperature of blood upstream of the heat exchanger is taken as the temperature of the patient's body taken at an extravascular location.

18. A method according to claim 16 wherein the temperature of blood downstream of the heat exchanger is measured in the pulmonary artery.

19. A method according to claim 16 wherein the temperature of blood upstream of the heat exchanger is the temperature of blood flowing through the vessel in which the heat exchanger is positioned, taken at a location upstream of the heat exchanger.

20. A method according to claim 16 wherein the temperature of blood upstream of the heat exchanger is the temperature of blood flowing through a vessel other than the vessel in which the heat exchanger is positioned.

21. A method for determining blood flow rate in a mammalian patient and for heating or cooling at least a portion of the patient's body, said method comprising the steps of:
A) providing a catheter having a beat exchange device that is useable to change the temperature of at least a portion of the patient's body;
B) inserting the heat exchange catheter into the vasculature of the patient and positioning the heat exchanger within a blood vessel;
C) causing heat to be exchanged between the heat exchanger and blood flowing past the heat exchanger so as to bring about a change in the temperature of all or a portion of the patient's body;
D) determining the amount of heat exchanged between the heat exchanger and the blood within a time period;
E) determining the temperature of blood flowing through the blood vessel upstream of the heat exchanger;
F) determining the temperature of blood flowing through the blood vessel downstream of the heat exchanger; and,
G) determining the flow rate of blood in the vessel based on the amount of heat exchanged between the heat exchanger and the blood and the difference between the temperature of blood upstream of the heat exchanger and the temperature of blood downstream of the heat exchanger;

the amount of heat exchanged between the heat exchanger and the blood in Step D being determined by the formula:

$$q = m \cdot (t_{in} - t_{out}) K$$

wherein q=heat exchange, m=flow rate of heat exchange fluid through the heat exchanger, $t_{in}$=temperature of heat exchange fluid entering the heat exchanger, $t_{out}$=temperature of heat exchange fluid exiting the heat exchanger and K=the thermal constant of the heat exchanger fluid.

22. A method according to claim 21 wherein the flow rate of blood through the vessel is determined in Step G by the formula:

Flow Rate per Time Period=Heat Exchanged÷Δ$t$ wherein Heat Exchanged=the amount of heat added to or removed from the blood per unit time and Δt=the difference between the temperature of the patient's blood before it undergoes heat exchange with the heat exchanger as measured by a second temperature measuring device and the temperature of blood flowing after it undergoes heat exchange the heat exchanger through the patient's pulmonary artery as measured by a first temperature measuring device.

23. A method for determining blood flow rate in a mammalian patient and for heating or cooling at least a portion of the patient's body, said method comprising the steps of:
A) providing a catheter having a heat exchange device that is useable to change the temperature of at least a portion of the patient's body;
B) inserting the heat exchange catheter into the vasculature and positioning the heat exchanger within a blood vessel;
C) causing heat to be exchanged between the heat exchanger and blood flowing past the heat exchanger so as to bring about a change in the temperature of all or a portion of the patient's body;
D) determining the amount of heat exchanged between the heat exchanger and the blood within a time period;
E) determining the temperature of blood flowing through the blood vessel upstream of the heat exchanger;
F) determining the temperature of blood flowing through the blood vessel downstream of the heat exchanger; and,
G) determining the flow rate of blood in the vessel based on the amount of heat exchanged between the heat exchanger and the blood and the difference between the temperature of blood upstream of the heat exchanger and the temperature of blood downstream of the heat exchanger, the flow rate of blood through the vessel being determined by the formula:

Flow Rate per Time Period=Heat Exchanged÷Δ$t$ wherein Heat Exchanged=the amount of heat added to or removed from the blood per unit time and Δt=the difference between the temperature of the patient's blood before it undergoes heat exchange with the heat exchanger as measured by a second temperature measuring device and the temperature of blood flowing through the patient's pulmonary artery as measured by a first temperature measuring device.

24. A method according to claim 23 wherein the amount of heat exchanged between the heat exchanger and the blood is determined in Step D by the formula:

$$q = m \cdot (t_{in} - t_{out}) K$$

wherein q=heat exchange, m=flow rate of heat exchange fluid through the heat exchanger, $t_{in}$=temperature of heat exchange fluid entering the heat exchanger, $t_{out}$=temperature of heat exchange fluid exiting the heat exchanger and K=the thermal constant of the heat exchanger fluid.

25. A method for determining cardiac output or discerning a substantial change in cardiac output in a mammalian patient, the method comprising the steps of:
   A) providing a heat exchange catheter that comprises an elongate catheter body having a heat exchanger positioned thereon;
   B) inserting the heat exchange catheter into the vasculature and positioning the heat exchanger within a blood vessel through which the blood flow rate is substantially the same as or bears a known relationship to cardiac output in that the luminal diameter of the vessel is estimated based on the height and weight of the patient;
   C) causing heat to be exchanged between the heat exchanger and blood flowing past the heat exchanger;
   D) determining the amount of heat exchanged between the heat exchanger and the blood within a time period;
   E) determining the flow rate of blood past the heat exchanger based on the amount of heat exchanged in the time period; and,
   F) computing at least an estimate of cardiac output or discerning a change in cardiac output, on the basis of the flow rate determined in Step E,
   wherein the luminal diameter of the vessel in which the heat exchanger is positioned is estimated based on the height and weight of the patient.

26. A method according to claim 25 wherein Step C is carried out such that the amount of heat exchanged between the heat exchanger and the blood results in a change in the temperature of all or part of a patient's body so as to induce hypothermia, induce hyperthermia, maintain normothermia or achieve and maintain a temperature that is different from that patient's normothermic temperature.

27. A method according to claim 25 wherein the flow rate of blood is determined in Step E by reference to a database which correlates flow rate values to corresponding amounts of heat exchange measured in Step D for blood in vessels having different luminal diameters.

28. A method according to claim 25 wherein the flow rate of blood is determined in Step E by the following formula:

$$CO = \text{Heat Exchanged} \div \Delta t$$

wherein CO=the amount of blood passing through the right heart per unit time, Heat Exchanged=the amount of heat added to or removed from the blood per unit time and $\Delta t$=the difference between the temperature of the patient's blood before it undergoes heat exchange with the heat exchanger and the temperature of blood $$CO = \text{Heat Exchanged} \div \Delta t$$

wherein CO=the amount of blood passing through the right heart per unit time, Heat Exchanged=the amount of heat added to or removed from the blood per unit time and $\Delta t$=the difference between the temperature of the patient's blood before it undergoes heat exchange with the heat exchanger and the temperature of blood flowing after it undergoes heat exchange with the heat exchanger.

29. A method according to claim 25 wherein the heat exchanger is positioned in the venous vasculature and wherein a computed or estimated cardiac output is calculated in Step F by multiplying the flow rate determined in Step E by a factor representing the portion of total venous blood flow through the right heart that comes from the vessel in which the heat exchanger is positioned.

30. A method for determining cardiac output or discerning a substantial change in cardiac output in a mammalian patient, the method comprising the steps of:
   A) providing a heat exchange catheter that comprises an elongate catheter body having a heat exchanger positioned thereon;
   B) inserting the heat exchange catheter into the vasculature and positioning the heat exchanger within a blood vessel through which the blood flow rate is substantially the same as or bears a known relationship to cardiac output;
   C) causing heat to be exchanged between the heat exchanger and blood flowing past the heat exchanger;
   D) determining the amount of heat exchanged between the heat exchanger and the blood within a time period;
   E) determining the flow rate of blood past the heat exchanger based on the amount of heat exchanged in the time period;
   F) computing at least an estimate of cardiac output or discerning a change in cardiac output, on the basis of the flow rate determined in Step E; and
   G) measuring the luminal diameter of the vessel in which the heat exchanger is positioned.

31. A method according to claim 30 wherein the luminal diameter of the vessel in which the heat exchanger is positioned is measured on an image of the vessel obtained by an imaging technique selected from the group consisting of:
   fluoroscopy;
   ultrasound imaging;
   intravascular ultrasound imaging;
   magnetic resonance imaging;
   computed tomographic imaging;
   angiography; and,
   X-ray.

32. A method according to claim 30 wherein Step C is carried out such that the amount of heat exchanged between the heat exchanger and the blood results in a change in the temperature of all or part of a patient's body so as to induce hypothermia, induce hyperthermia, maintain normothermia or achieve and maintain a temperature that is different from that patient's normothermic temperature.

33. A method for determining cardiac output or discerning a substantial change in cardiac output in a mammalian patient, the method comprising the steps of:
   A) providing a heat exchange catheter that comprises an elongate catheter body having a heat exchanger positioned thereon;
   B) inserting the heat exchange catheter into the venous vasculature and positioning the heat exchanger within a blood vessel through which the blood flow rate is substantially the same as or bears a known relationship to cardiac output;
   C) causing heat to be exchanged between the heat exchanger and blood flowing past the heat exchanger;
   D) determining the amount of heat exchanged between the heat exchanger and the blood within a time period;
   E) determining the flow rate of blood past the heat exchanger based on the amount of heat exchanged in the time period; and,
   F) computing at least an estimate of cardiac output by multiplying the flow rate determined in Step E by a factor representing the portion of total venous blood flow through the heart that comes from the vessel in which the heat exchanger is positioned, or discerning a change in cardiac output, on the basis of the flow rate determined in Step E.

34. A method according to claim 33 wherein at least a portion of the heat exchanger is positioned in the inferior vena cava and the factor applied for that portion of the heat exchanger is approximately ⅔.

35. A method according to claim 33 wherein at least a portion of the heat exchanger is positioned in the inferior vena cava and the factor applied for that portion of the heat exchanger is approximately ⅓.

36. A method according to claim 33 wherein at least a portion of the heat exchanger is positioned in the right atrium and the factor applied for that portion of the heat exchanger is 100%.

37. A method for determining cardiac output or discerning a substantial change in cardiac output in a mammalian patient, the method comprising the steps of:
 A) providing a heat exchange catheter that comprises an elongate catheter body having a heat exchanger through which a heat exchange fluid is circulated, positioned thereon;
 B) inserting the heat exchange catheter into the vasculature and positioning the heat exchanger within a blood vessel through which the blood flow rate is substantially the same as or bears a known relationship to cardiac output;
 C) causing heat to be exchanged between the heat exchanger and blood flowing past the heat exchanger;
 D) determining the amount of heat exchanged between the heat exchanger and the blood within a time period, the amount of heat exchanged being calculated based on the amount of power consumed by an external unit;
 E) determining the flow rate of blood past the heat exchanger based on the amount of heat exchanged in the time period; and
 F) computing at least an estimate of cardiac output or discerning a change in cardiac output, on the basis of the flow rate determined in Step E.

38. A method according to claim 37 wherein the amount of heat exchanged between the heat exchanger and the blood is determined by the formula:

$$q = m \cdot (t_{in} - t_{out}) K$$

wherein q=heat exchange, m=flow rate of heat exchange fluid through the heat exchanger, $t_{in}$=temperature of heat exchange fluid entering the heat exchanger, $t_{out}$=temperature of heat exchange fluid exiting the heat exchanger and K=the thermal constant of the heat exchanger fluid.

39. A method for determining cardiac output or discerning a substantial change in cardiac output in a mammalian patient, the method comprising the steps of:
 A) providing a heat exchange catheter that comprises an elongate catheter body having a heat exchanger positioned thereon;
 B) inserting the heat exchange catheter into the vasculature and positioning the heat exchanger within a blood vessel through which the blood flow rate is substantially the same as or bears a known relationship to cardiac output;
 C) causing heat to be exchanged between the heat exchanger and blood flowing past the heat exchanger;
 D) determining the amount of heat exchanged between the heat exchanger and the blood within a time period;
 E) determining the flow rate of blood past the heat exchanger based on the amount of heat exchanged in the time period;
 F) computing at least an estimate of cardiac output or discerning a change in cardiac output, on the basis of the flow rate determined in Step E;
 G) measuring the temperature of blood downstream of the heat exchanger; and
 H) measuring the temperature of blood upstream of the heat exchanger;
 wherein the amount of heat exchanged in the time period is determined in Step D by the formula:

$$\text{downstream temperature} - \text{upstream temperature}.$$

40. A method according to claim 39 wherein the temperature of blood downstream of the heat exchanger is measured in the pulmonary artery.

41. A method according to claim 39 wherein the temperature of blood upstream of the heat exchanger is the temperature of blood flowing through the vessel in which the heat exchanger is positioned, taken at a location upstream of the heat exchanger.

42. A method according to claim 39 wherein the temperature of blood upstream of the heat exchanger is the temperature of blood flowing through a vessel other than the vessel in which the heat exchanger is positioned.

43. A method according to claim 39 wherein the temperature of blood upstream of the heat exchanger is taken as the temperature of the patient's body taken at an extravascular location.

* * * * *